(12) United States Patent
Yamazaki et al.

(10) Patent No.: US 6,433,168 B1
(45) Date of Patent: Aug. 13, 2002

(54) HIGHLY PURE PHENOTHIAZINE COMPOUND, PRODUCTION METHOD THEREOF, PRODUCTION METHOD OF INTERMEDIATE THEREFOR, AND HYDRATE AND NOVEL CRYSTAL AS STARTING MATERIALS FOR THE INTERMEDIATE

(75) Inventors: Shigeya Yamazaki; Hiroyuki Yumoto; Masami Igi, all of Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/621,782

(22) Filed: Jul. 21, 2000

(30) Foreign Application Priority Data

Jul. 26, 1999 (JP) ............................................. 11-211310
Nov. 11, 1999 (JP) ............................................. 11-321786

(51) Int. Cl.$^7$ ............................................. C07D 417/00
(52) U.S. Cl. ............................................. 544/43; 544/46
(58) Field of Search ............................................. 544/43, 46

(56) References Cited

U.S. PATENT DOCUMENTS

| | | | |
|---|---|---|---|
| 3,725,410 A | 4/1973 | Potoski et al. | 260/268 BC |
| 3,792,053 A | 2/1974 | Potoski et al. | 260/288 R |
| 4,855,290 A | 8/1989 | Fisher et al. | 514/278 |
| 4,876,260 A | 10/1989 | Fisher et al. | 514/278 |
| 5,691,349 A | 11/1997 | Mallion et al. | 514/305 |

FOREIGN PATENT DOCUMENTS

| | | |
|---|---|---|
| FR | 2 772 029 | 6/1999 |
| JP | 04 169583 | 6/1992 |
| JP | 05 140157 | 6/1993 |

OTHER PUBLICATIONS

Iki et al., "Preparation of Phenothiazine Derivatives as Intermediates for the Known Antihistaminic Mequitazine," Chemical Abstracts 120(1), 8602q (Jan. 3, 1994) (XP–002156429).
Patent Abstract: JP 05 140157 (Jun. 8, 1993).
Iki et al., "Preparation of Phenothiazine Derivatives," Chemical Abstracts, 118 (1), 6983z (Jan. 4, 1993) (XP–002156430).
Patent Abstract: JP 61 280497 (Dec. 11, 1986).
Patent Abstract: JP 02 062883 (Mar. 3, 1989).
Itoh et al., "Hazardous Properties of Reaction Products of Dimethyl Sulfoxide–Sodium Hydride Dispersion," Safe Engineering, 23 (5), 269–275 (1984).

*Primary Examiner*—Richard L. Raymond
*Assistant Examiner*—Kahsay Habte
(74) *Attorney, Agent, or Firm*—Leydig, Voit & Mayer, Ltd.

(57) ABSTRACT

According to the method of the present invention, an alkali metal compound, dimethyl sulfoxide, trimethyloxosulfonium halide and 3-quinuclidinone are added in a specific order to give the following compound [II]. This compound is, without treatment or isolation, directly reacted with an alkali metal salt of phenothiazine to give the following compound [III], from which the following compound [I] is obtained. During the production of compound [I], a by-produced acidic gas is removed and water is added to ensure industrial, safe and efficient production of compound [I] at a constantly high yield. Inasmuch as the present invention enables production of the following highly pure compound [A] by eliminating hydrogen halide of compound [I] in glyme in the presence of at least one kind of a base selected from potassium hydroxide and potassium alkoxide, compound [A] having a high purity of not less than 85 mol % can be provided.

24 Claims, 7 Drawing Sheets

HIGHLY PURE PHENOTHIAZINE COMPOUND, PRODUCTION METHOD THEREOF, PRODUCTION METHOD OF INTERMEDIATE THEREFOR, AND HYDRATE AND NOVEL CRYSTAL AS STARTING MATERIALS FOR THE INTERMEDIATE

TECHNICAL FIELD OF THE INVENTION

The present invention relates to (E)-10-(1-azabicyclo[2.2.2]oct-3-ylidenemethyl)phenothiazine of the formula [A]

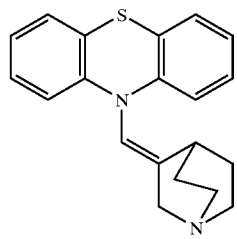

[A]

which is a synthetic intermediate for pharmaceutically useful mequitazine having antihistaminic action and the like, and which has a purity of not less than 85 mol % (hereinafter to be also referred to as compound [A]) and a production method thereof. In addition, the present invention relates to a production method of a compound of the formula [I]

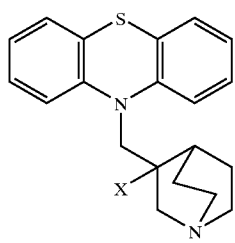

[I]

wherein X is a halogen atom, which is an intermediate for the above-mentioned compound [A], (hereinafter to be also referred to as compound [I]), and to a hydrate and a novel crystal of compound [III], which are used for the production of compound [I].

BACKGROUND OF THE INVENTION

The mequitazine of the following formula

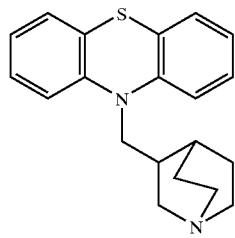

is a pharmaceutically useful substance having various actions such as antihistaminic action, cholinergic action-inhibitory action, antiadrenergic action, neurosedative action, ataractic action, spasmolytic action and the like. Mequitazine can be produced by the following reaction

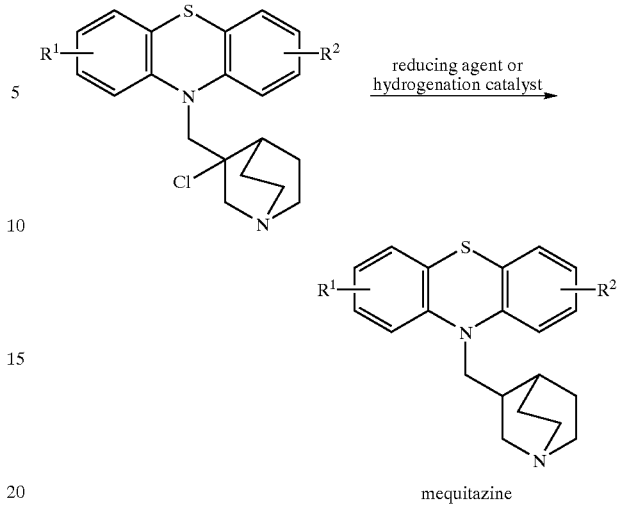

werein $R^1$ and $R^2$ are the same or different and each is hydrogen atom, halogen atom, alkyl, alkoxy or alkylthio, in which 10-(3-chloro-1-azabicyclo[2.2.2]oct-3-ylmethyl)phenothiazine is reduced in the presence of a reducing agent or hydrogenation catalyst to give mequitazine (JP-B-2835413).

According to this method, the reaction proceeds at a high temperature. Up-scaling, therefore, leads to the occurrence of thermal decomposition and elimination of hydrogen halide. This in turn causes degradation of the quality and yield of mequitazine, the need for column purification and hydrogenation, and the like. For use at an industrial level, therefore, an improvement is essential. When a boron compound is used as a reaction reagent, moreover, an adduct of the product and boron is generated, which requires addition of an acid (e.g., acetic acid) and heat treatment of the mixture.

Other production method of mequitazine may be the following series of reactions:

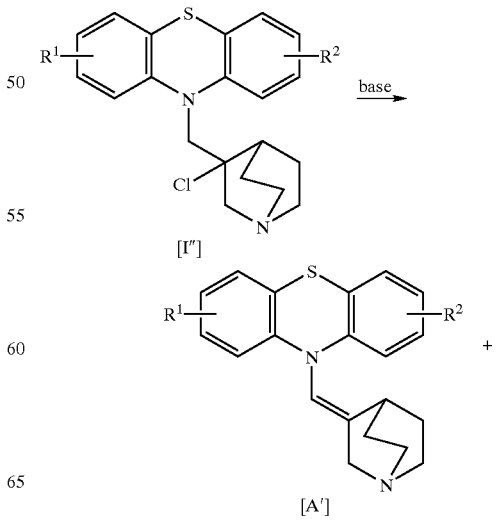

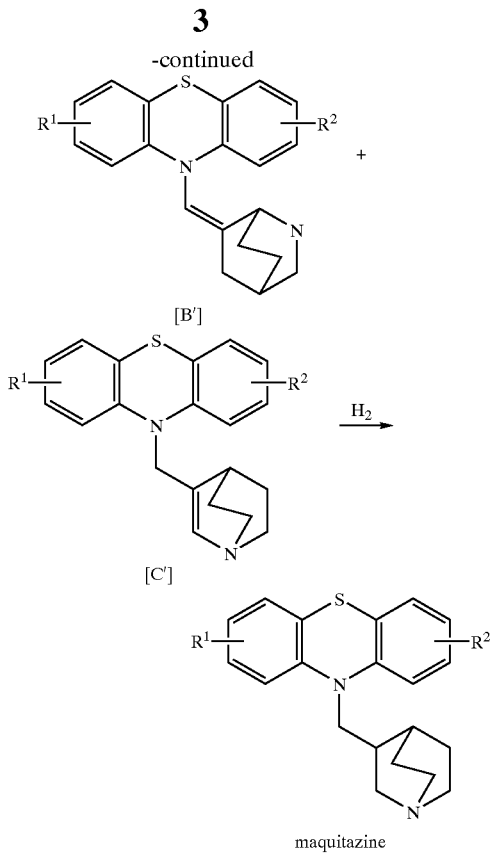

maquitazine wherein $R^1$ and $R^2$ are as defined above (JP-A-5-140157). According to this method, 10-(3-chloro-1-azabicyclo[2.2.2]oct-3-ylmethyl)phenothiazine is subjected to elimination of hydrogen halide in an inert solvent in the presence of a base, such as hydroxide, hydride or alcholate of an alkali metal, to give three kinds of intermediates, which are hydrogenated without separation to produce mequitazine. In this method, hydrogenation is carried out using an expensive hydrogenation catalyst, such as palladium carbon, in the same amount as the intermediate, thereby resulting in higher production costs.

In view of such situation, there has been a demand for a method for industrial production of mequitazine at a high purity, a high yield and at a lower cost.

According to the present invention, it has been found with regard to the above-mentioned three kinds of intermediates (compound [A'], compound [B'], compound [C']) as disclosed in JP-A-5-140157, that, of the compounds wherein $R^1$ and $R^2$ are hydrogen atoms [compound [A], (Z)-10-(1-azabicyclo[2.2.2]oct-3-ylidenemethyl)phenothiazine (hereinafter to be also referred to as compound [B]) and 10-(1-azabicyclo[2.2.2]oct-2-en-3-ylmethyl)phenothiazine (hereinafter to be also referred to as compound [C]), respectively], compound [B] is hardly subject to hydrogenation, and that compound [C], which is most susceptible to hydrogenation among the three kinds of intermediates, suffers from lower purity and lower yield when reacted under the conditions that selectively afford this compound, that is, the reaction of 10-(3-chloro-1-azabicyclo[2.2.2]oct-3-ylmethyl)phenothiazine and alkali metal alcholate in an alcohol solvent, because 10-(3-alkoxy-1-azabicyclo[2.2.2]oct-3-ylmethyl)phenothiazine is by-produced. In addition, it has been found that compound [A] is susceptible to hydrogenation and that this compound is most suitable as a synthetic intermediate for mequitazine.

In short, the present inventors have found that production of compound [A] at a high purity is most beneficial for the production of mequitazine.

Compound [I] is useful as a starting material for compound [A]. Compound [I] can be obtained by reacting 3-methylenequinuclidine oxide of the formula [II]

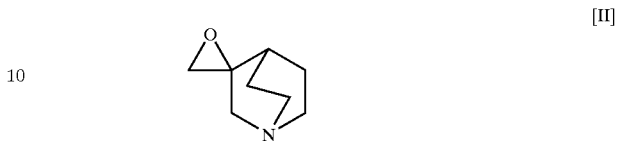

hereinafter to be also referred to as Compound [II], and an alkali metal salt of phenothiazine (JP-B-2835413). 3-Methylene-quinuclidine oxide to be used as a starting material can be produced by a known synthetic method (U.S. Pat. No. 3,725,410, U.S. Pat. No. 3,792,053, JP-A-61-280497, JP-A-2-62883) via dimsyl sodium. However, dimsyl sodium is unstable and dangerous (*Anzen Kogaku* (Safe Engineering) Vol. 23, No. 5, 269–274 (1984)).

In JP-A-61-280497, Example 1. (a)–(ii), teaches how to scale up the production of 3-methylenequinuclidine oxide. In this Example, a dispersion of toluene, 3-quinuclidinone, trimethyloxo-sulfonium iodide and sodium hydride in paraffin is charged and then dimethyl sulfoxide is added dropwise. According to this method, sodium hydride and trimethyloxosulfonium iodide are added in advance and dimethyl sulfoxide is subsequently added. As a result, dimethyl sulfoxide reacts with sodium hydride to form dimsyl sodium, and then dimsyl sodium reacts with trimethyloxosulfonium iodide to form dimethyloxosulfonium methylide as well as dimethyl sulfoxide. In other words, the addition of even a single drop of dimethyl sulfoxide in this method theoretically results in the completion of the reaction, because it generates dimethyl sulfoxide which automatically reacts successively with previously-added sodium hydride. *Anzen Kogaku*, ibid, teaches the instability of this reaction system by stating that a dimsyl sodium solution placed under adiabatic conditions at 55° C. for 5 hr moves on to a runaway reaction. In fact, a reproductive testing of the method of JP-A-61-280497 in a reaction vessel of a 2000 L level ended up in carbonization of the contents due to a runaway reaction occurred therein. To conclude, this method allows reaction of dimsyl sodium immediately after formation thereof, but once dimethyl sulfoxide is added, the above-mentioned series of reactions occur, thereby producing dimethyl sulfoxide, and the newly-generated dimethyl sulfoxide causes another cycle of the above-mentioned reactions. This makes termination of the reaction difficult, and the reaction heat causes run away of the reaction due to the autoexothermicity of dimsyl sodium, to the degree that the reaction may induce an explosion. An enlarged reaction scale increases the risk of explosion.

In Example 1(II) of JP-A-61-280497, 3-quinuclidinone is reacted with dimethyloxosulfonium methylide, and the resulting reaction mixture of 3-methylenequinuclidine oxide is poured into water and subjected to extraction with chloroform for post-treatment. This method includes a loss in the amount of the final product, which loss becomes even greater by the concentration after extraction. 3-Methylenequinuclidine oxide isolated by the method disclosed in this publication and an alkali metal salt of phenothiazine were condensed to give 10-(3-hydroxy-1-azabicyclo[2.2.2]oct-3-ylmethyl)phenothiazine of the formula [III]

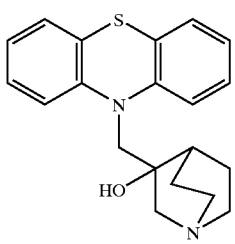

[III]

(hereinafter to be also referred to as Compound [III]) only at an unstable yield of 0–50%. This is because 3-methylenequinuclidine oxide cannot be isolated at a constant percentage, the method includes a great loss as mentioned above, and because extraction solvent chloroform remains from isolation and forms carbene with the alkali metal, causing resinification. Consequently, the compound [III] cannot be obtained at a constantly high yield.

In Example 2 of JP-B-2835413, compound [III] was reacted with phosphorus oxychloride in monochlorobenzene at 110–120° C. for 13 hr to give compound [I] at a yield of 44%. In this reaction, higher reaction temperatures result in greater amounts of resinified components, thereby degrading hue and yield, but lower reaction temperatures improve hue and yield to a greater degree. For a higher yield to be achieved, therefore, refluxing in a solvent having a lower boiling point, such as 1,2-dichloroethane (bp 83° C.) and chloroform (bp 61° C.), may be employed. On the contrary, however, the use of these solvents should be avoided in consideration of a possible influence on human body and the environment.

There has been a demand for an industrially safe method of producing compound [I] efficiently and at a constantly high yield from 3-quinuclidinone via compound [II] and compound [III].

It is therefore an object of the present invention to provide compound [A] having a high purity, and a production method of this compound. Another object of the present invention to provide an industrially safe method of producing compound [I] efficiently and at a constantly high yield from 3-quinuclidinone via compound [II] and compound [III]. It is a still yet object of the present invention to provide a hydrate and a novel crystal of compound [III].

SUMMARY OF THE INVENTION

Such objects can be achieved by the present invention described in the following.

According to the present invention, an alkali metal compound, dimethyl sulfoxide, trimethyloxosulfonium halide and 3-quinuclidinone or a salt thereof are added in a specific order to produce 3-methylenequinuclidine oxide from 3-quinuclidinone industrially safely even at an enlarged scale. To be specific, dimethyl sulfoxide, trimethyloxosulfonium halide and 3-quinuclidinone or a salt thereof are charged in advance, and then an alkali metal compound is added to inhibit generation of dimsyl sodium. Dimsyl sodium thus produced immediately reacts with trimethyloxosulfonium halide to produce dimethyloxosulfonium methylide and 3-methylenequinuclidine oxide. Inasmuch as trimethyloxosulfonium halide is added to the reaction system in advance, unstable dimsyl sodium regarded as risk-carrying can be used for the reaction immediately after formation, and by the successive addition of an alkali metal compound, dimsyl sodium can be inhibited from being generated, which in turn enables industrially safe production of 3-methylenequinuclidine oxide.

When 3-methylenequinuclidine oxide produced according to the above-mentioned method is directly reacted with an alkali metal salt of phenothiazine without treatment or isolation, namely, by carrying out from the generation of 3-methylenequinuclidine oxide to the generation of compound [III] in one pot, compound [III] can be obtained at a constantly high yield.

When compound [I] is obtained from compound [III], a by-produced acidic gas is removed to promote the reaction, whereby the reaction temperature can be lowered and the reaction time can be shortened. When compound [I] is obtained from compound [III], water is added to promote the reaction.

By the above steps, compound [I] can be produced industrially safely, efficiently and stably at a high yield from 3-quinuclidinone via compound [II] and compound [III].

When compound [I] is subjected to elimination of hydrogen halide in glyme in the presence of at least one kind of a base selected from the group consisting of potassium hydroxide and potassium alkoxide, compound [A] having a high purity of not less than 85 mol % can be produced.

DETAILED DESCRIPTION OF THE INVENTION

Figure 1:
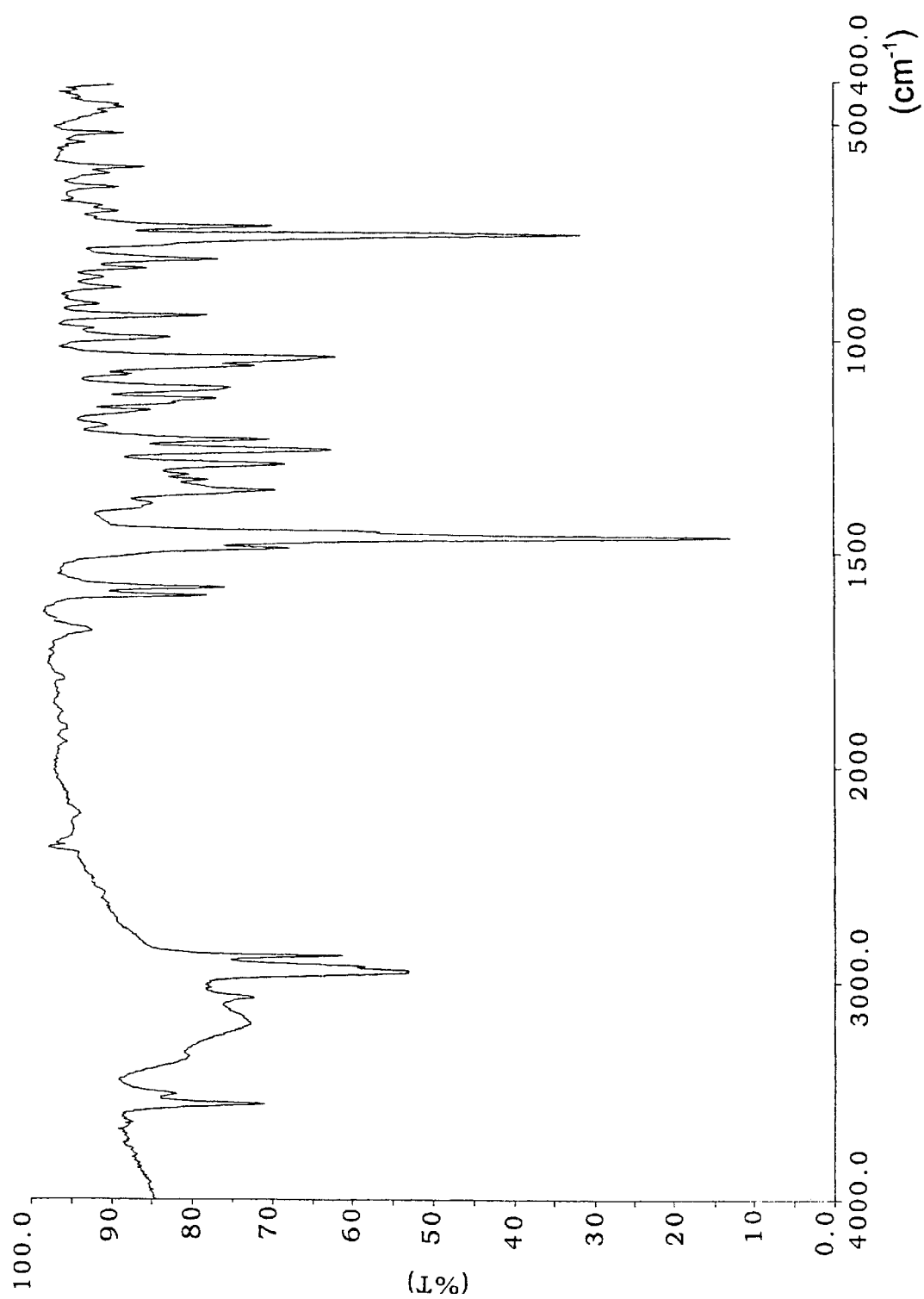
FIG. 1 shows an infrared absorption spectrum of the compound obtained in Example 6.

The present invention is explained in detail in the following by referring to (1) a production method (Step 1) of compound [II], (2) a method (Step 2) for producing compound [III] from compound [II], (3) a method (Step 3) for producing compound [I] from compound [III], (4) a production method of compound [A], and (5) a production method of mequitazine.

Step 1

In Step 1, an alkali metal compound is added to a mixture containing dimethyl sulfoxide, 3-quinuclidinone or a salt thereof, and trimethyloxosulfonium halide to produce compound [II].

In this Step, the addition of an alkali metal compound starts the reaction. Since trimethyloxosulfonium halide has been added to the reaction system in advance, the addition of the alkali metal compound produces dimsyl sodium from dimethyl sulfoxide, which dimsyl sodium immediately reacts with trimethyloxosulfonium halide. The progress of this reaction can be controlled by changing the amount and rate of the addition of the alkali metal compound, which in turn ensures safe production of compound [II]. The alkali metal compound is the key compound to initiate the reaction in the present invention, and it is essential that this compound not be contained in the above-mentioned mixture.

To be specific, for example, dimethyl sulfoxide and trimethyloxosulfonium halide are added to a mixture of 3-quinuclidinone or salt thereof and a reaction solvent, and then an alkali metal compound is added to produce compound [II].

In Step 1, the alkali metal compound is preferably added successively in portions, more preferably added in portions as a solid, or added dropwise as a suspension in a solvent inert to the alkali metal compound, from the aspect of safety of the reaction. As used herein, by "added successively" is meant continuous or intermittent addition of the alkali metal compound in portions in an amount necessary for the reaction, that permits control of the reaction rate, without a particular limitation on the form (e.g., solid, liquid, etc.) of the alkali metal compound at the time of addition.

By the addition of the alkali metal compound in portions as a solid is meant addition of the alkali metal compound to be used for the reaction after dividing the amount of the compound into portions that permit control of the reaction rate. The number of the portions varies depending on the reaction scale. For example, when the reaction scale is of a laboratory level, such as 500–2000 ml, the alkali metal compound is preferably divided into 5–20 portions, more preferably 10–15 portions, and when the reaction scale is of an industrial level (2000–5000 L), the alkali metal compound is preferably divided into 10–30 portions, more preferably 15–20 portions, and added over 1–12 hr, more preferably 2–6 hr.

By the dropwise addition of the alkali metal compound as a suspension in a solvent inert to the alkali metal compound is meant that the alkali metal compound is prepared into a suspension in the following solvent inert to the compound and the suspension is added at a rate that permits control of the reaction rate. The time of dropwise addition depends on the reaction scale. For example, when the reaction scale is 0.5 L–5000 L, the compound is preferably added dropwise over 1–12 hr, more preferably 2–6 hr. The solvent inert to the alkali metal compound is free of any particular limitation as long as it allows an alkali metal compound to suspend therein and to be added dropwise in a slurry state. Examples thereof include hydrocarbons such as liquid paraffin, heptane, hexane, benzene, toluene, xylene and the like, with preference given to liquid paraffin. The solvent is used in such an amount that makes a slurry and that permits dropwise addition of the slurry of the alkali metal compound, such as 1–5 parts by weight, more preferably 2–3 parts by weight, per part by weight of the alkali metal compound.

Examples of trimethyloxosulfonium halide to be used in Step 1 include trimethyloxosulfonium iodide, trimethyloxosulfonium chloride and trimethyloxosulfonium bromide, with preference given to trimethyloxosulfonium iodide. The amount of use of trimethyloxosulfonium halide is 1.0- to 1.5-fold, preferably 1.0- to 1.3-fold, molar amount relative to 3-quinuclidinone or a salt thereof.

3-Quinuclidinone to be used in Step 1 is generally available from the market in the form of a salt. Examples of the salt of 3-quinuclidinone include inorganic acid salt (e.g., hydrochloride, hydrobromide, sulfate etc.) of 3-quinuclidinone and organic acid salt (e.g., acetate, methanesulfonate etc.) of 3-quinuclidinone. In the case of a salt of 3-quinuclidinone, it may be used for the reaction after liberation or used in the form of a salt by using an excess alkali metal compound.

Examples of preferable alkali metal compound to be used in Step 1 include alkali metal hydride (e.g., sodium hydride, potassium hydride etc.) and alkali metal alkoxide (e.g., potassium tert-butoxide, sodium tert-butoxide, sodium methoxide, potassium methoxide etc.), with more preference given to sodium hydride and potassium tert-butoxide, with particular preference given to sodium hydride. Sodium hydride may be a commercially available product which is a dispersion in a mineral oil.

When a salt of 3-quinuclidinone is liberated and then used for the reaction, the alkali metal compound is preferably used in an amount of 1.0- to 1.5-fold, more preferably 1.05- to 1.3-fold, molar amount relative to the salt of 3-quinuclidinone for an improved reaction rate, and 1.0- to 1.05-fold molar amount relative to the salt of 3-quinuclidinone for ensured safety.

When a salt of 3-quinuclidinone is used for the reaction without liberation, the alkali metal compound is used in the total of the amount necessary for the reaction and an amount of liberated salt of 3-quinuclidinone. For example, 2.0- to 3.0-fold molar amount, more preferably 2.1- to 2.6-fold molar amount, of alkali metal compound is used relative to 1 molar amount of the salt of 3-quinuclidinone.

In Step 1, dimethyl sulfoxide functions as a reaction reagent and reaction solvent. The amount of dimethyl sulfoxide as a reaction reagent is 0.1- to 15-fold molar amount, preferably 3- to 6-fold molar amount, relative to 1 molar amount of 3-quinuclidinone or a salt thereof.

The reaction solvent to be used in Step 1 may be dimethyl sulfoxide alone or a mixed solvent of dimethyl sulfoxide and a solvent inert to the reaction. Examples of the solvent inert to the reaction include toluene, tetrahydrofuran (THF), xylene, benzene and the like. The preferable reaction solvent may be dimethyl sulfoxide alone or a mixed solvent of dimethyl sulfoxide and toluene. The reaction solvent is used in an amount of 0.5–20 L, preferably 1.5–15 L, per 1 kg of 3-quinuclidinone or a salt thereof.

The temperature and the conditions for a smooth progress of the reaction in Step 1 are as follows. The alkali metal compound is added at 0–80° C., preferably 10–60° C. After the addition of alkali metal compound, the reaction is carried out at 0–80° C., preferably 10–60° C., for 1–5 hr, preferably 1–2 hr. The reaction preferably proceeds in the presence of an inert gas such as nitrogen gas.

Step 2

In Step 2, compound [II] is reacted with an alkali metal salt of phenothiazine to produce compound [III]. Step 2 is preferably carried out directly after Step 1 without treatment of the reaction mixture or isolation of compound [II]. To be specific, an alkali metal compound is added to the mixture containing dimethyl sulfoxide, 3-quinuclidinone or a salt thereof, and trimethyloxosulfonium halide in Step 1, and an alkali metal salt of phenothiazine is preferably added directly to the resulting reaction mixture. Alternatively, the reaction mixture obtained in Step 1 is preferably added to an alkali metal salt of phenothiazine to allow reaction. This is because compound [II] is unstable. By carrying out the reaction in one pot from Step 1, unstable compound [II] can be immediately condensed with phenothiazine, whereby the yield of compound [III] can be increased and the yield is stabilized.

The preferable alkali metal salt of phenothiazine to be used in Step 2 is exemplified by potassium salt of phenothiazine and sodium salt of phenothiazine, which is used in an amount of 1.0- to 2.0-fold, preferably 1.1- to 1.3-fold molar amount, relative to compound [II]. The alkali metal salt of phenothiazine may be added as a mixture with a solvent. The solvent may be any as long as it is inert to the reaction in Step 2, and may be toluene, xylene, hexane, methanol, ethanol, THF, dioxane, ethyl acetate, monochlorobenzene, dichlorobenzene, dichloromethane, dichloroethane or a mixed solvent thereof, with preference given to toluene because it is inert to the condensation with compound [II] and it requires no post-treatment. The solvent is used in an amount of 2–15 L, preferably 3–7 L, relative to 1 kg of phenothiazine.

The alkali metal salt of phenothiazine can be obtained by reacting phenothiazine with an alkali metal compound (e.g., potassium tert-butoxide, potassium hydroxide, sodium hydride, sodium amide etc.) in the above-mentioned solvent.

The reaction in Step 2 is generally carried out at a temperature within the range of from room temperature to 150° C. for 30 minutes to 20 hr. A higher reaction temperature in Step 2 makes the reaction rate faster. For a shortened reaction time, the reaction is preferably carried out at 90–120° C. However, since heat is generated in the early stage of reaction, the reaction is preferably carried out at 70–120° C.

Compound [III] can be isolated and purified by a conventional method such as concentration, extraction, column chromatography, reprecipitation, recrystallization and the like.

While compound [III] has not been so far obtained in the form of a hydrate, the present inventors have first found that it can be obtained as a hydrate by (i) drying the wet crystals of compound [III] at a low temperature or by (ii) drying the crystals at a high temperature into an anhydride and leaving the anhydride in the atmosphere having a certain humidity.

The low temperature in (i) above means 20–50° C., preferably 20–40° C., the high temperature in (ii) above means 80–130° C., preferably 90–120° C. The humidity is subject to no particular limitation, but it is preferably 40–100%, more preferably 60–100%, and the time of standing is 6–72 hr, preferably 12–24 hr. The formation of a hydrate can be confirmed by measuring the water content of the obtained compound, that should correspond to the water content of a hydrate, by, for example, Karl Fischer method, and subjecting the compound to DSC measurement to obtain a pattern similar to the one shown in FIG. 2.

Conventionally, compound [III] is obtained as crystals by dissolving in water and adding alkali to allow crystal precipitation. The present inventors have obtained novel crystals that are different from conventionally obtained crystals, and that show a peak in a DSC curve between 143° C. and 145° C. The present inventors have found that the novel crystals can be obtained by crystallization from the following organic solvent.

To be specific, the novel crystals can be obtained by, for example, crystallization of compound [III] from the following organic solvent used in an amount of 2–15 L, preferably 3–6 L, per 1 kg of compound [III]. The organic solvent for this end is exemplified by toluene, xylene, benzene, dichloromethane, chloroform, ethyl acetate, monochlorobenzene; a mixed solvent of these and a hydrocarbon solvent (e.g., hexane, heptane and the like); and the like, with preference given to a mixed solvent of toluene and heptane, toluene and monochlorobenzene.

Step 3

In Step 3, compound [III] is reacted with a halogenation agent in a reaction solvent to give compound [I]. The halogen atom at X of formula [I] may be, for example, fluorine atom, chlorine atom, bromine atom or iodine atom, with preference given to chlorine atom.

In Step 3, removal of acidic gas by-produced from the reaction system is preferable for a higher yield and from the aspect of industrial advantages, because it leads to the promotion of reaction, lower reaction temperature and shorter reaction time. In this Step, addition of water to the reaction system is also preferable because it accelerates the reaction. The reaction between compound [III] and a halogenation agent more preferably proceeds in the presence of water while removing the by-produced acidic gas from the reaction system.

The method for removing the by-produced acidic gas from the reaction system may be a method comprising introducing an inert gas into the reaction system or a method comprising refluxing the reaction mixture under reduced pressure, with preference given to the introduction of an inert gas into the reaction system because this method can be applied to many reaction systems.

The method for introducing an inert gas into the reaction system may be a method comprising flowing an inert gas in the gaseous phase of the reaction system or a method comprising bubbling the gas into the reaction mixture. The inert gas is exemplified by nitrogen gas, argon gas, helium gas and the like, with preference given to nitrogen gas. The inert gas need only be introduced during the reaction in an amount sufficient to remove the acidic gas from the reaction system. This method can be employed when a reaction solvent has a relatively lower boiling point and can be also applied to many reaction systems. The method for refluxing the reaction mixture under reduced pressure means a reaction carried out while reducing the pressure to remove the by-produced acidic gas.

In Step 3, compound [III] is added to a reaction solvent, and a halogenation agent is added, preferably by dropwise addition, to give compound [I]. Water can be added concurrently with the addition of compound [III], wherein compound [III] may be a hydrate.

The halogenation agent to be used in Step 3 is subject to no particular limitation as long as it can achieve the object of the present invention, and may be phosphorus oxychloride, thionyl chloride, phosphorus pentachloride, phosphorus tribromide, thionyl bromide and the like. These halogenation agents may be used alone or in combination. Phosphorus oxychloride is preferably used, because it can lower the reaction temperature. The amount of the halogenation agent to be used is generally 1- to 10-fold molar amount, preferably 1.5- to 3.0-fold molar amount, relative to compound [III]. When its amount is less than equimolar amount, the reaction rate becomes lower to result in insufficient halogenation. When it exceeds 10-fold molar amount, the reaction rate becomes faster, but the post-treatment becomes complicated and an economical problem arises.

The reaction solvent to be used in Step 3 is subject to no particular limitation as long as it is inert to the reaction in Step 3. For example, those used in Step 2 can be used, with articular preference given to monochlorobenzene. When phosphorus oxychloride is used as the halogenation agent, the reaction solvent is preferably monochlorobenzene, o-dichlorobenzene or chloroform, particularly preferably monochlorobenzene. The amount of the reaction solvent is generally such an amount as dissolves the entire starting material compound and the entire reaction product, compound [I].

A preferable combination of a reaction solvent, a halogenation agent and an inert gas is that of monochlorobenzene (reaction solvent), phosphorus oxychloride (halogenation agent) and nitrogen gas (inert gas to be introduced into the reaction system).

When water is to be added to the reaction system, the amount thereof varies depending on the kind of the halogenation agent. For example, when phosphorus oxychloride is used as the halogenation agent, the amount of water is 0.1- to 1.25-fold molar amount, preferably 0.5-fold molar amount to equimolar amount, relative to phosphorus oxychloride. The amount of water is 0.5- to 3-fold molar amount relative to compound [III]. When compound [III] is used in the form of a hydrate, the amount of water contained in the hydrate should be included in the above-mentioned amount of water.

The reaction temperature in Step 3 is generally from room temperature to 150° C. at normal pressure, and when addition of water or removal of by-produced acidic gas from the reaction system is involved, it is generally from room temperature to 150° C., preferably 70° C.–100° C. The reaction time in Step 3 is generally 8–72 hr, preferably 12–24 hr. When addition of water or removal of by-produced acidic gas from the reaction system is involved, it is generally 6–48 hr, preferably 10–20 hr.

The compound [I] can be isolated by a conventional method, which includes, for example, treating a reaction mixture with an aqueous alkaline solution, concentrating the obtained organic layer and precipitating compound [I] from a suitable solvent. The compound [I] can be purified by a conventional method such as recrystallization and the like.

Production Method of Compound [A]

The compound [A] of the present invention having a purity of not less than 85 mol % means that a substance contains compound [A] in a molar percentage of not less than 85. The substance may be any as long as it contains compound [A] in this proportion. The compound contained in the substance besides compound [A] is subject to no particular limitation.

In the present invention, compound [A] has a purity of not less than 85 mol %, preferably not less than 95 mol %. One example of the production method to obtain compound [A] having a purity of not less than 85 mol % is shown in the following.

In JP-A-5-140157, compound [A] is obtained along with compound [B] and compound [C] in the following scheme, by the elimination of hydrogen halide by the use of 10-(3-chloro-1-azabicyclo[2.2.2]oct-3-ylmethyl)phenothiazine (compound of following formula [I']) as a starting material in an inert solvent in the presence of a base.

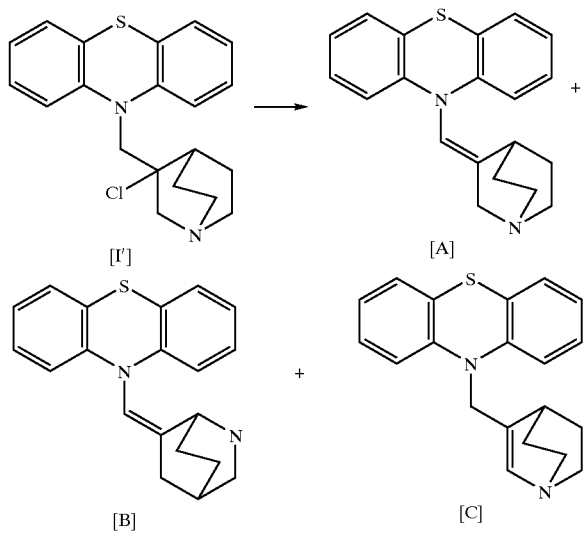

The present inventors used glyme as an inert solvent and at least one kind of potassium hydroxide and potassium alkoxide as a base in the reaction disclosed in the above-mentioned publication and found that compound [A] can be obtained at a high purity. That is, compound [A] can be obtained at a high purity by subjecting compound [I] to the elimination of hydrogen halide in glyme in the presence of at least one kind of base selected from the group consisting of potassium hydroxide and potassium alkoxide.

To be specific, compound [I] is added to a suspension of the above-mentioned specific base in glyme and the mixture is subjected to elimination of hydrogen halide at a given temperature for a given time, whereby compound [A] can be obtained at a high yield and a high purity. In this case, the suspension obtained by adding the above-mentioned specific base to glyme may be heated before adding compound [I], but the temperature of the liquid is preferably set to 5° C. or below to achieve a high yield.

Examples of the glyme, which is a reaction solvent for the production of compound [A], include monoglyme, diglyme, triglyme, tetraglyme and the like, which is preferably monoglyme, diglyme, with more preference given to diglyme. The reaction solvent is used in an amount of 1- to 30-fold parts by weight, preferably 2- to 20-fold parts by weight, relative to compound [I]. The reaction solvent may be a mixed solvent containing a different solvent as long as it does not adversely affect the reaction. Examples of the different solvent include toluene, xylene, monochlorobenzene, o-dichlorobenzene, m-dichlorobenzene and the like.

The specific base to be used for the production of compound [A] is potassium hydroxide or potassium alkoxide. Examples of potassium alkoxide include linear or branched chain potassium alkoxide having 1 to 4 carbon atoms, such as potassium methoxide, potassium ethoxide, potassium isopropoxide, potassium tert-butoxide and the like, with preference given to potassium tert-butoxide. These may be used alone or in combination. A base preferable for the production of compound [A] is potassium hydroxide or potassium tert-butoxide. The base is used in an amount of 1- to 10-fold molar amount, preferably 1.1- to 5-fold molar amount, relative to compound [I].

Compound [A] is produced generally by the reaction at 0–150° C. for 30 min–40 hr, preferably at 20–80° C. for 1–30 hr.

The termination of the reaction for the production of compound [A] can be confirmed by high performance liquid chromatography (HPLC) based on the disappearance or decrease of compound [I]. Compound [A] can be isolated as crystals by, for example, adding a suitable amount of water to the reaction mixture after the completion of the reaction and subjecting the mixture to recrystallization. The obtained crystals are taken out and used for the next Step (synthesis of mequitazine by hydrogenation) without drying.

By the production method of the above-mentioned compound [A], compound [B] and compound [C] are also obtained. While compound [A] is generated as the main component, this can be confirmed by subjecting the reaction mixture after the completion of the reaction and before isolation to HPLC. The residue after evaporation of the solvent contains the objective compound [A] in a proportion of not less than 85 mol %, preferably not less than 95 mol %.

The obtained compound [A] can be introduced into mequitazine which is a pharmaceutically useful compound having various actions such as antihistaminic action, cholinergic action-inhibitory action, antiadrenergic action, neurosedative action, ataractic action, spasmolytic action and the like.

Production Method of Mequitazine

Mequitazine can be obtained by, for example, reducing compound [A] with hydrogen gas in a solvent inert to the hydrogenation in the presence of a hydrogenation catalyst (JP-A-5-140157). Addition of a protonic acid (e.g., acetic acid, propionic acid and the like) to the reaction system in an amount of 1- to 5-fold molar amount, preferably 1.2- to 3-fold molar amount, relative to compound [A] is preferable because it raises the reaction rate. The amount of hydrogen gas to be used for the reaction is an equimolar amount relative to compound [A].

The solvent inert to hydrogenation is, for example, methanol, ethanol, glyme (e.g., monoglyme, diglyme etc.), water, a mixed solvent of toluene and methanol, and the like, with preference given to methanol and diglyme. The solvent is used in an amount of 1- to 30-fold parts by weight, preferably 2- to 20-fold parts by weight, relative to compound [A].

For the production of mequitazine, a hydrogenation catalyst may be further added. The hydrogenation catalyst is subject to no particular limitation as long as it is a typical one. Examples thereof include platinum black, colloidal platinum, platinum oxide, palladium carbon, palladium/calcium carbonate, palladium/barium sulfate, Raney catalyst such as nickel, cobalt, iron and the like, nickel/kieselguhr, copper chromite and the like, with preference given to palladium carbon. The amount of the hydrogenation catalyst to be used varies depending on the kind thereof, and when, for example, palladium carbon is used, the amount thereof relative to compound [A] is 1–100 wt %, preferably 5–15 wt %, by conversion to a dry product, and 0.1–10 wt %., preferably 0.5– 1.5 wt %, by conversion to a metal.

Mequitazine is produced under the atmospheric pressure, preferably under pressurization, wherein the pressurization means generally about 2–10 kg/cm$^2$. The reaction temperature is 0–150° C., preferably 30–60° C., and the reaction time is 1–24 hr, preferably 6–10 hr.

After the completion of the reaction, a conventional method, such as filtration, recrystallization and the like, can isolate mequitazine. When highly pure compound [A] is used as the starting material, the amount of expensive hydrogenation catalyst conventionally used in the same amount as the starting material can be reduced, while still producing highly pure mequitazine at a high yield.

The present invention is explained in detail in the following by referring to illustrative examples. The present invention is not limited by these examples in any way.

REFERENCE EXAMPLE 1

Synthesis of 3-quinuclidinone

99% Sodium hydroxide (97.0 g, 2.4 mol) was dissolved in water (285 ml) and 3-quinuclidinone hydrochloride (193.9 g, 1.2 mol) was added. The mixture was extracted with toluene (600 ml). The obtained aqueous layer was re-extracted with toluene (300 ml). The obtained toluene layer was combined with the toluene layer obtained previously and the mixture was dried over anhydrous magnesium sulfate and concentrated to give a toluene solution (438.1 g) containing 3-quinuclidinone (150.2 g, yield: 100%).

REFERENCE EXAMPLE 2

Synthesis of Phenothiazine Potassium Salt

Phenothiazine (46.0 g, 0.231 mol) and potassium tert-butoxide (25.9 g, 0.231 mol) were added to toluene (280 ml), and the mixture was heated and refluxed for 1 hr. The by-produced tert-butanol was azeotropically evaporated with toluene while supplementally adding toluene until the temperature in the funnel reached the boiling point of toluene to give a slurry of phenothiazine potassium salt in toluene (yield: 100%).

REFERENCE EXAMPLE 3

Synthesis of Phenothiazine Potassium Salt

Phenothiazine (67.8 g, 0.33 mol) and 96% potassium hydroxide (21.2 g, 0.363 mol) were added to toluene (303 ml), and the mixture was heated and refluxed for 2 hr to give a slurry of phenothiazine potassium salt in toluene (yield: 100%).

REFERENCE EXAMPLE 4

Synthesis of Phenothiazine Sodium Salt

Phenothiazine (49.8 g, 0.25 mol) and 60% sodium hydride (9.6 g, 0.24 mol) were added to toluene (303 ml), and a small amount of DMF was added. The mixture was heated and ref luxed for 2 hr to give a slurry of phenothiazine sodium salt in toluene (yield: 100%).

REFERENCE EXAMPLE 5

Synthesis of Phenothiazine Potassium Salt

Phenothiazine (138.7 g, 0.696 mol) and potassium tert-butoxide (78.1 g, 0.696 mol) were added to toluene (905 ml), and the mixture was heated and refluxed for 1 hr at 100–106° C. The by-produced tert-butanol was azeotropically evaporated with toluene while supplementally adding toluene until the temperature in the funnel reached the boiling point of toluene to give a slurry of phenothiazine potassium salt in toluene (yield: 100%).

EXAMPLE 1

Synthesis of 10-(3-hydroxy-1-azabicyclo[2.2.2]oct-3-ylmethyl)phenothiazine (Synthesis of compound [III] via compound [II])

3-Quinuclidinone (23.2 g, 0.185 mol) was dissolved in toluene (51 ml), and trimethyloxosulfonium iodide (48.9 g, 0.222 mol) and dimethyl sulfoxide (154.7 g, 1.98 mol) were added. Thereto was dropwise added a suspension of 60% sodium hydride (8.16 g, sodium hydride: 0.204 mol) in 16.3 ml of liquid paraffin at 25–34° C. over 1 hr, and the dropping funnel after dropwise addition was washed with liquid paraffin (4.1 ml) to remove residual suspension into the resulting mixture. During the addition, generation of hydrogen in an amount corresponding to the dropwise added sodium hydride was observed. After stirring the mixture at 26–30° C. for 1 hr 30 min, the termination of the reaction was confirmed by GC (gas chromatography) to give a solution of 3-methylenequinuclidine oxide in a mixture of dimethyl sulfoxide-toluene.

The slurry of phenothiazine potassium salt in toluene obtained in Reference Example 2 was added. The mixture was heated and refluxed for 1 hr (115–120° C.). The reaction mixture was cooled to about 70° C. and water (230 ml) was added to partition the reaction mixture. Water (230 ml) was further added and the mixture was washed with the added water. The mixture was partitioned. The title compound was extracted with water (111 ml) and acetic acid (12.2 g, 0.203 mol) from the obtained toluene layer into the aqueous layer, and the aqueous layer was washed with toluene (46 ml).

Separately, 99% sodium hydroxide (8.59 g, 0.213 mol) was dissolved in water (139 ml) and the solution was heated to 80–90° C. The obtained aqueous layer was added dropwise at the same temperature over 1 hr 30 min. After aging for 30 min, the reaction mixture was cooled, filtrated, washed with water (92.5 ml), and dried to give the title compound (47.1 g, 0.139 mol, yield 75.3%, melting point:127–130° C.).

EXAMPLE 2

Synthesis of 10-(3-hydroxy-1-azabicyclo[2.2.2]oct-3-ylmethyl)phenothiazine (Synthesis of compound [III] via compound [II])

3-Quinuclidinone (23.2 g, 0.185 mol) was dissolved in toluene (51 ml) and trimethyloxosulfonium iodide (40.7 g, 0.185 mol) and dimethyl sulfoxide (154.7 g, 1.98 mol) were added. Thereto was dropwise added a suspension of 63% sodium hydride (7.03 g, sodium hydride: 0.185 mol) in 14.1 ml of liquid paraffin at 26–35° C. over 1 hr 30 min, and the dropping funnel after dropwise addition was washed with liquid paraffin (3.5 ml) to remove residual suspension into the resulting mixture. During the addition, generation of hydrogen in an amount corresponding to the dropwise added sodium hydride was observed. After stirring the mixture at 26–30° C. for 2 hr, the termination of the reaction was confirmed by GC to give a solution of 3-methylenequinuclidine oxide in a mixture of dimethyl sulfoxide-toluene.

The slurry of phenothiazine potassium salt in toluene obtained in Reference Example 2 was added. The mixture was heated and refluxed for 1 hr (115–120° C.). The reaction mixture was cooled to about 70° C. and water (230 ml) was added to partition the reaction mixture. Water (230 ml) was further added and the mixture was washed with the added water. The mixture was partitioned. The title compound was extracted with water (111 ml) and acetic acid (12.2 g, 0.203 mol) from the obtained toluene layer into the aqueous layer, and the aqueous layer was washed with toluene (46 ml).

Separately, 99% sodium hydroxide (8.59 g, 0.213 mol) was dissolved in water (139 ml) and the solution was heated to 80–90° C. The obtained aqueous layer was added dropwise at the same temperature over 1 hr. After aging for 30 min, the reaction mixture was cooled, filtrated, washed with water (92.5 ml), and dried to give the title compound (44.5 g, 0.131 mol, yield 71.0%, melting point: 127–130° C.).

EXAMPLE 3

Synthesis of 10-(3-hydroxy-1-azabicyclo[2.2.2]oct-3-ylmethyl)phenothiazine (Synthesis of compound [III] via compound [II])

3-Quinuclidinone (23.2 g, 0.185 mol) was dissolved in toluene (51 ml) and trimethyloxosulfonium iodide (49.0 g, 0.222 mol) and dimethyl sulfoxide (155.2 g, 1.98 mol) were added. Thereto was added 60% sodium hydride (8.25 g, sodium hydride:0.206 mol) in portions at 24–30° C. over 1 hr 40 min. During the divided addition, generation of hydrogen in an amount corresponding to the added sodium hydride was observed. After stirring the mixture at 27° C. for 2 hr, the termination of the reaction was confirmed by GC to give a solution of 3-methylenequinuclidine oxide in a mixture of dimethyl sulfoxide-toluene.

The slurry of phenothiazine potassium salt in toluene obtained in Reference Example 2 was added. The mixture was heated and refluxed for 1 hr (115–120° C.). The reaction mixture was cooled to about 65° C. and water (233 ml) was added to partition the reaction mixture. Water (233 ml) was further added and the mixture was washed with the added water. The mixture was partitioned. The title compound was extracted with water (111 ml) and acetic acid (12.3 g, 0.204 mol) from the obtained toluene layer into the aqueous layer, and the aqueous layer was washed with toluene (46 ml).

Separately, 99% sodium hydroxide (9.13 g, 0.226 mol) was dissolved in water (139 ml) and the solution was heated to 80–90° C. The obtained aqueous layer was added dropwise at the same temperature over 30 min. After aging for 30 min, the reaction mixture was cooled, filtrated, washed with water (93 ml), and dried to give the title compound (44.1 g, 0.130 mol, yield 70.2%, melting point: 127–130° C.).

EXAMPLE 4

Synthesis of 10-(3-hydroxy-1-azabicyclo[2.2.2]oct-3-ylmethyl)phenothiazine (Synthesis of compound [III] via compound [II])

3-Quinuclidinone (23.2 g, 0.185 mol) was dissolved in toluene (51 ml) and trimethyloxosulfonium iodide (49.0 g, 0.222 mol) and dimethyl sulfoxide (155.2 g, 1.98 mol) were added. Thereto was dropwise added a suspension of 63% sodium hydride (8.17 g, sodium hydride:0.215 mol) in 16.3 ml of liquid paraffin at 25–30° C. over 14 min, and the dropping funnel after dropwise addition was washed with liquid paraffin (4.1 ml) to remove residual suspension into the resulting mixture. During the addition, generation of hydrogen in an amount corresponding to the dropwise added sodium hydride was observed. After stirring the mixture at 25–30° C. for 1 hr, the termination of the reaction was confirmed by GC to give a solution of 3-methylenequinuclidine oxide in a mixture of dimethyl sulfoxide-toluene.

The slurry of phenothiazine potassium salt in toluene as obtained in Reference Example 2 was added. The mixture was heated and refluxed for 1 hr (115–120° C.). The reaction mixture was cooled to about 65° C. and water (233 ml) was added to partition the reaction mixture. Water (233 ml) was further added and the mixture was washed with the added water. The mixture was partitioned. The title compound was extracted with water (111 ml) and acetic acid (12.3 g, 0.204 mol) from the obtained toluene layer into the aqueous layer, and the aqueous layer was washed with toluene (46 ml).

Figure 5:
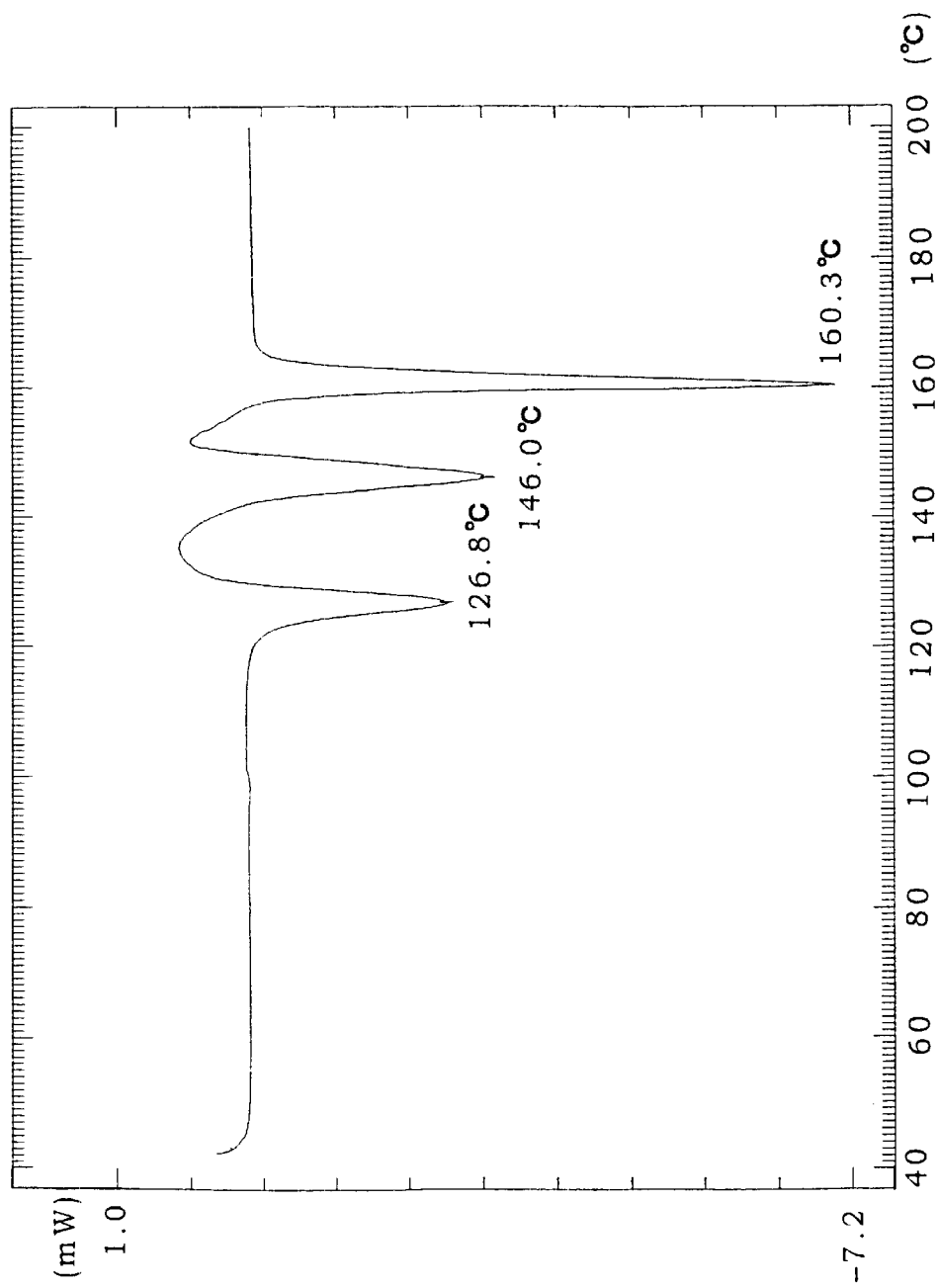
FIG. 5 shows a DSC curve of the compound obtained in Example 4.
Figure 6:
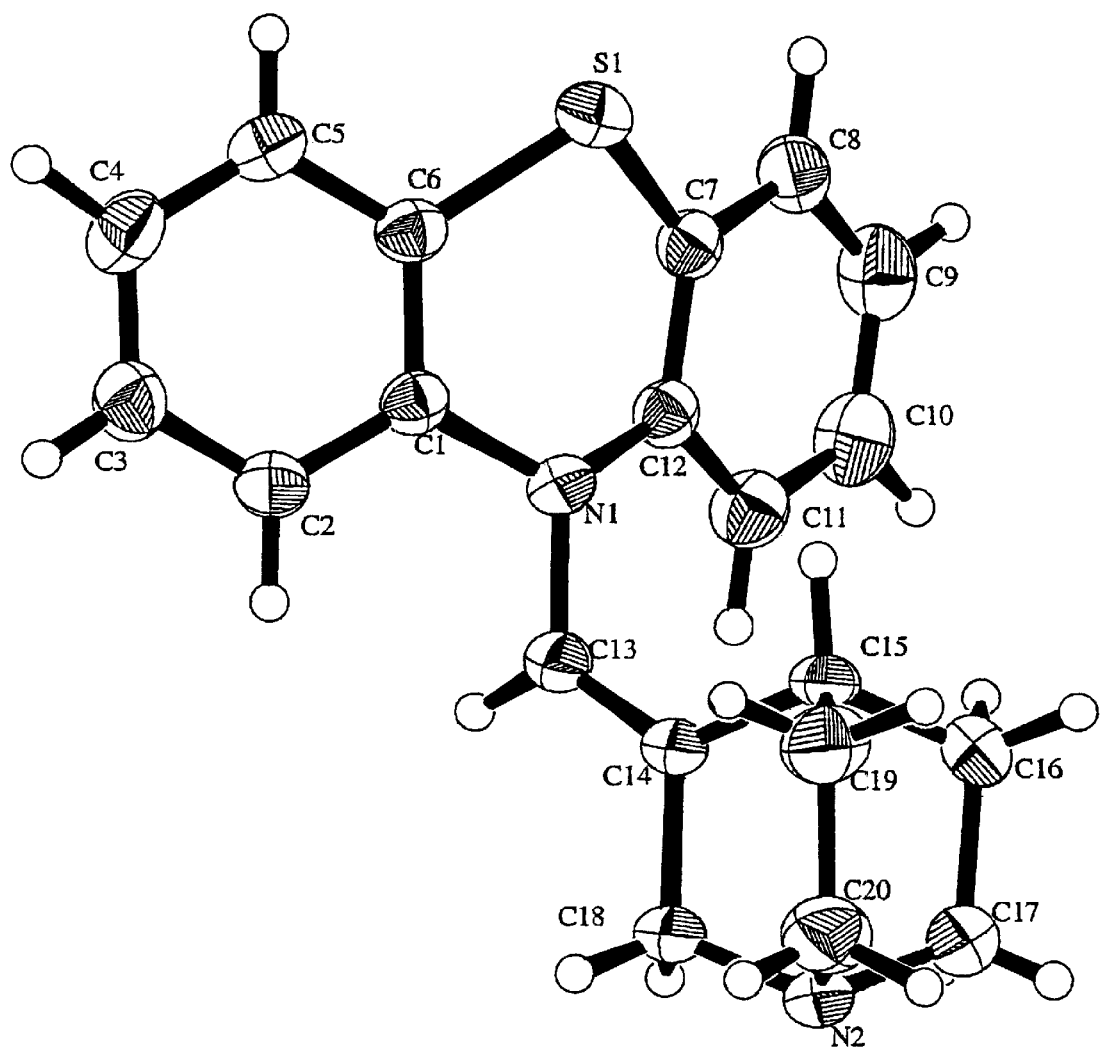
FIG. 6 shows the structure of the compound obtained in Example 14, which has been determined by X-ray crystal diffraction analysis.
Figure 7:
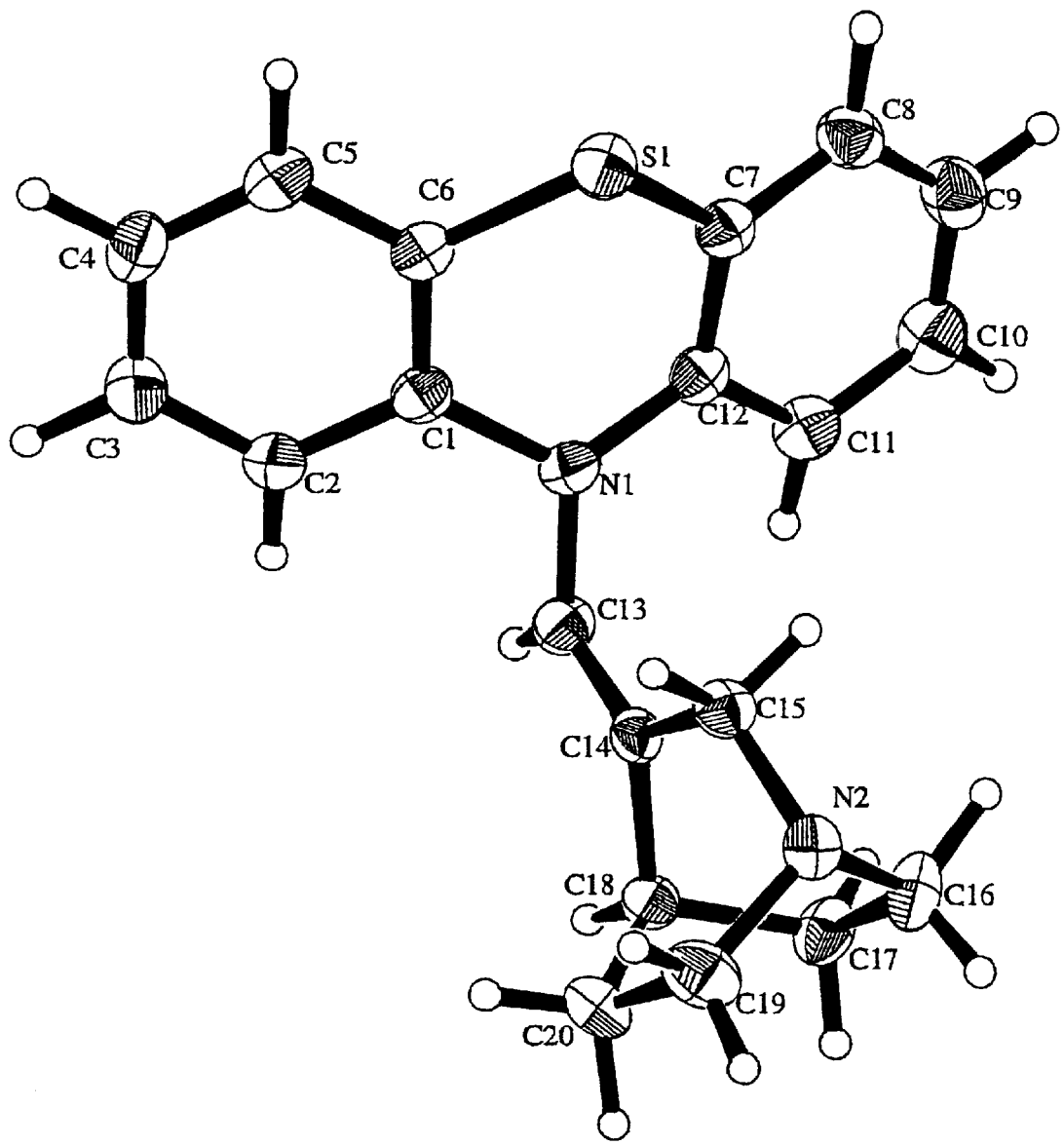
FIG. 7 shows the structure of the compound obtained in Comparative Example 2, which has been determined by X-ray crystal diffraction analysis.

Separately, 99% sodium hydroxide (8.63 g, 0.213 mol) was dissolved in water (139 ml) and the solution was heated to 80–90° C. The obtained aqueous layer was added dropwise at the same temperature over 30 min. After aging for 30 min, the reaction mixture was cooled, filtrated, washed with water (93 ml), and dried to give the title compound (45.0 g, 0.133 mol, yield 71.5%, melting point: 127–130° C.). The results of DSC measurement are shown in FIG. 5.

EXAMPLE 5

Synthesis of 10-(3-hydroxy-1-azabicyclo[2.2.2]oct-3-ylmethyl)phenothiazine (Synthesis of compound [III] via compound [II])

3-Quinuclidinone (69.7 g, 0.557 mol) was dissolved in toluene (154 ml) and trimethyloxosulfonium iodide (135.0 g, 0.613 mol) and dimethyl sulfoxide (466.0 g, 5.96 mol) were added. Thereto was dropwise added a suspension of 63% sodium hydride (21.4 g, sodium hydride:0.56 mol) in 43 ml of liquid paraffin at 25–30° C. under a nitrogen gas atmosphere over 6 hr, and the dropping funnel after dropwise addition was washed with liquid paraffin (43 ml) to remove residual suspension into the resulting mixture. During the addition, generation of hydrogen in an amount corresponding to the dropwise added sodium hydride was observed. After stirring the mixture at 25–30° C. for 1 hr, the termination of the reaction was confirmed by GC to give a solution of 3-methylenequinuclidine oxide in a mixture of dimethyl sulfoxide-toluene.

The slurry of phenothiazine potassium salt (0.696 mol) in toluene obtained in the same manner as in Reference Example 1 was added. The mixture was heated and refluxed for 1 hr (117–120° C.). The reaction mixture was cooled to about 65° C. and water (698 ml) was added to partition the reaction mixture. Water (698 ml) was further added and the mixture was washed with the added water. The mixture was partitioned. The title compound was extracted with water (501 ml) and acetic acid (40.1 g, 0.668 mol) from the obtained toluene layer into the aqueous layer, and the aqueous layer was washed with toluene (418 ml).

Separately, 99% sodium hydroxide (28.1 g, 0.696 mol) was dissolved in water (418 ml) and the solution was heated to 80–90° C. The obtained aqueous layer was added dropwise at the same temperature over 30 min. After aging for 30 min, the reaction mixture was cooled, filtrated, washed with water (278 ml), and dried to give the title compound (132.0 g, 0.390 mol, yield 70.0%, melting point: 127–130° C.).

EXAMPLE 6

Figure 2:
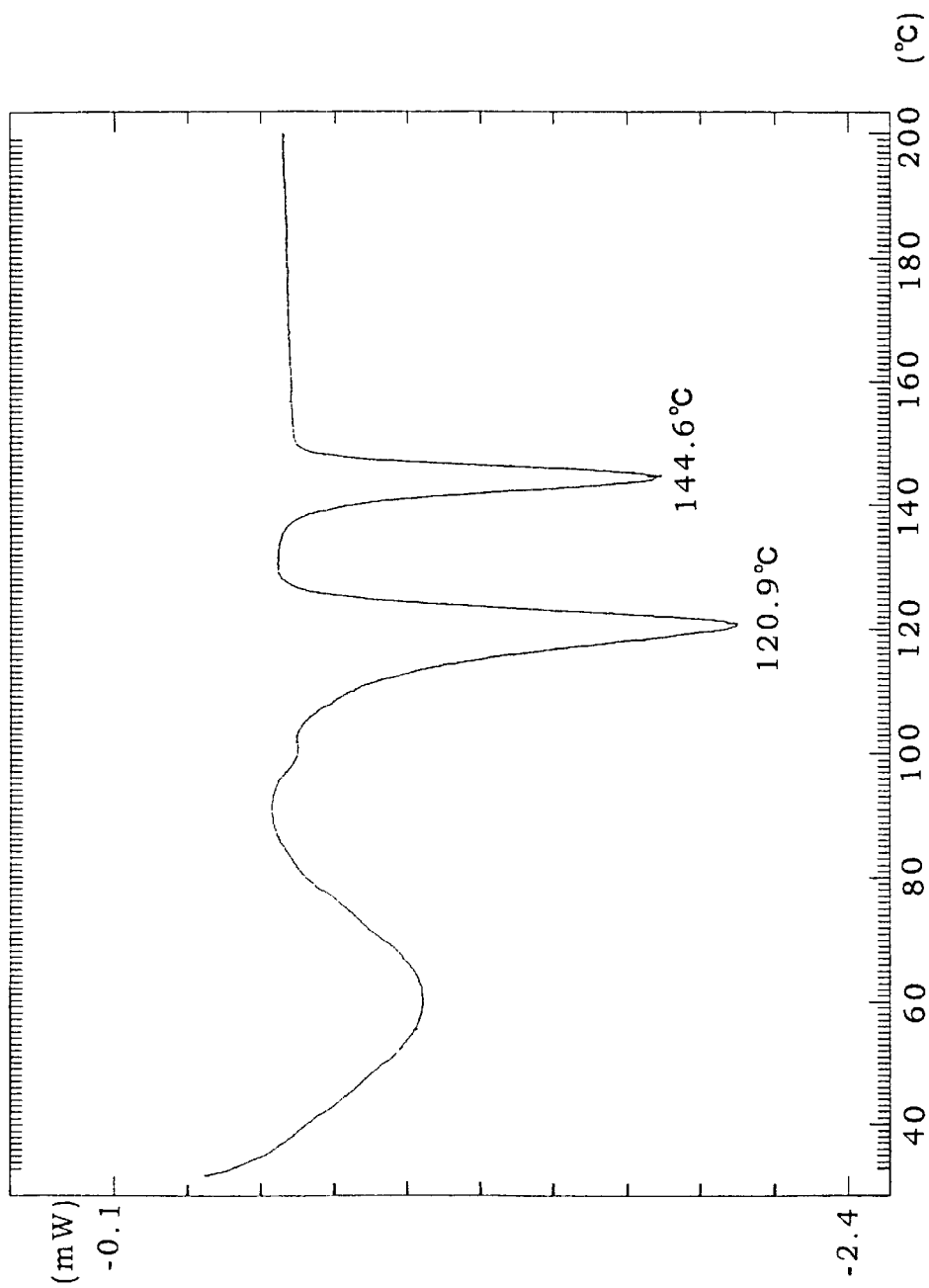
FIG. 2 shows a Differential Scanning Calorimetry (DSC) curve of the compound obtained in Example 6.

Synthesis of 10-(3-hydroxy-1-azabicyclo[2.2.2]oct-3-ylmethyl)phenothiazine Monohydrate The wet crystals of 10-(3-hydroxy-1-azabicyclo[2.2.2]oct-3-ylmethyl)phenothiazine obtained in Example 4 were dried at 90° C. for 12 hr. After confirmation of the generation of anhydride of the phenothiazine compound based on the water content of 0.1% and the same DSC measurement pattern as in FIG. 5, the compound was left standing in the atmosphere (humidity: 65%) for 22 hr. The obtained hydrate was measured for water content by the Karl Fischer method, which was found to be 4.8–5.1 wt %. The infrared absorption spectrum of the hydrate was measured (KBr method) and is shown in FIG. 1. The results of DSC measurement are shown in FIG. 2.
Elemental Analysis:
Calculated C=67.38, H=6.79(%) (=$C_{20}H_{24}N_2O_2S_1$)
Found C=67.45, H=6.66(%)

EXAMPLE 7

Figure 3:
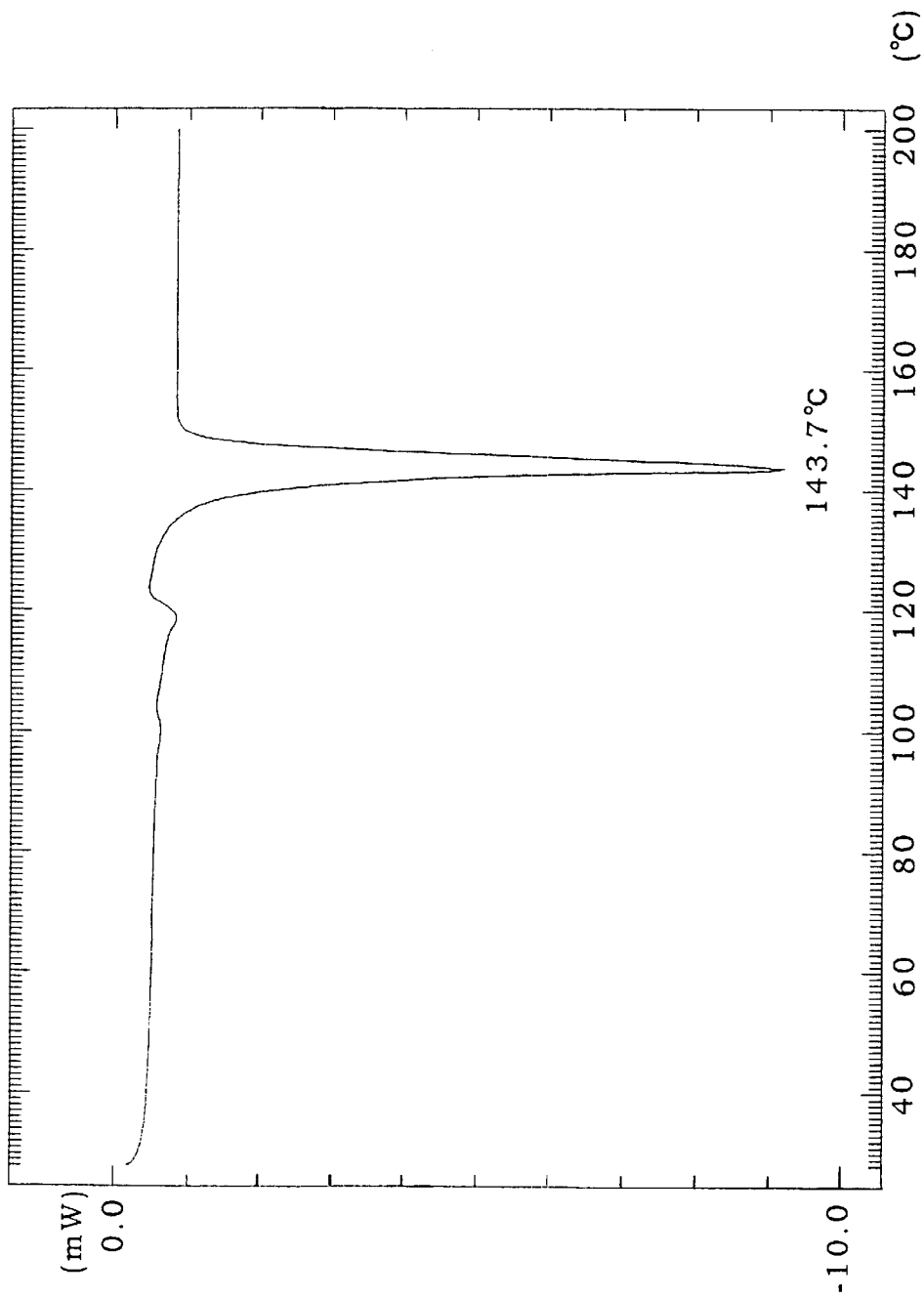
FIG. 3 shows a DSC curve of the compound obtained in Example 7.

Synthesis of Novel Crystals of 10-(3-hydroxy-1-azabicyclo[2.2.2]-oct-3-ylmethyl)phenothiazine 10-(3-Hydroxy-1-azabicyclo[2.2.2]oct-3-ylmethyl)phenothiazine (10.0 g) obtained in Example 4 was recrystallized from toluene (40 ml) to give the title compound (7.43 g). The results of DSC measurement are shown in FIG. 3.

EXAMPLE 8

Figure 4:
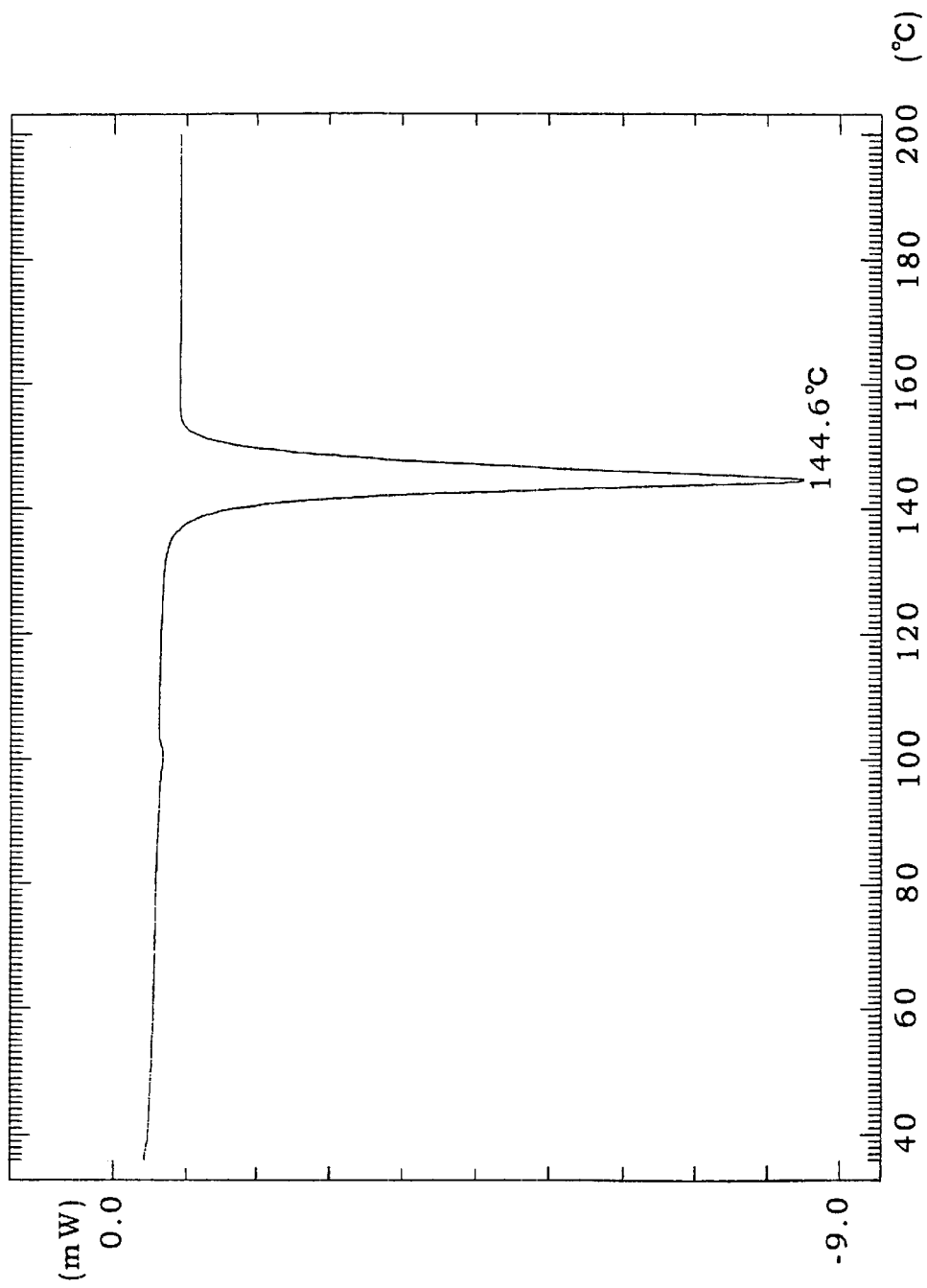
FIG. 4 shows a DSC curve of the compound obtained in Example 8.

Synthesis of Novel Crystals of 10-(3-hydroxy-1-azabicyclo[2.2.2]-oct-3-ylmethyl)phenothiazine 10-(3-Hydroxy-1-azabicyclo[2.2.2]oct-3-ylmethyl)phenothiazine (10.0 g) obtained in Example 4 was recrystallized from a mixed solvent of toluene (40 ml) and heptane (10 ml) to give the title compound (7.89 g). The results of DSC measurement are shown in FIG. 4.

EXAMPLE 9

Synthesis of Novel Crystals of 10-(3-hydroxy-1-azabicyclo[2.2.2]-oct-3-ylmethyl)phenothiazine 10-(3-Hydroxy-1-azabicyclo[2.2.2]oct-3-ylmethyl)phenothiazine (10.0 g) obtained in Example 4 was recrystallized from monochlorobenzene (30 ml) to give the title compound (7.12 g). The results of DSC measurement were the same as in Example 7.

EXAMPLE 10

Synthesis of 10-(3-chloro-1-azabicyclo[2.2.2]oct-3-ylmethyl)phenothiazine (Synthesis of compound [I])

10-(3-Hydroxy-1-azabicyclo[2.2.2]oct-3-ylmethyl)-phenothiazine (66.0 g, 0.195 mol) and water (5.27 g, 0.292 mol) were added to monochlorobenzene (660 ml), and phosphorus oxychloride (59.8 g, 0.390 mol) was added dropwise at 65–83° C. The mixture was heated, refluxed at 70–90° C. for 8 hr under reduced pressure, and the termination of the reaction was confirmed by HPLC.

Separately, 99% sodium hydroxide (47.3 g, 1.17 mol) was dissolved in water (165 ml) and the reaction mixture was added dropwise at 15–60° C. for hydrolysis. The obtained organic layer was treated with active charcoal (3.3 g) and concentrated. The concentrate was crystallized with diglyme (66 ml). After aging at 1–5° C. for 1 hr, the crystals were collected by filtration and dried to give the title compound (50.8 g, 0.142 mol, yield 73.1%, melting point:156–160° C.).

EXAMPLE 11

Synthesis of 10-(3-chloro-1-azabicyclo[2.2.2]oct-3-ylmethyl)phenothiazine (Synthesis of compound [I])

10-(3-Hydroxy-1-azabicyclo[2.2.2]oct-3-ylmethyl)phenothiazine (33.9 g, 0.1 mol) and water (2.70 g, 0.15 mol) were added to monochlorobenzene (220 ml), and phosphorus oxychloride (30.7 g, 0.2 mol) was added dropwise at 65–75° C. The mixture was heated, reacted at 84–85° C. for 18 hr in a stream of nitrogen at 20–25 ml/min, and the termination of the reaction was confirmed by HPLC.

Separately, 99% sodium hydroxide (24.2 g, 0.6 mol) was dissolved in water (85 ml) and the reaction mixture was added dropwise at 55–60° C. for hydrolysis. The obtained organic layer was treated with active charcoal (1.7 g) and concentrated. The concentrate was crystallized with diglyme (47 ml). After aging at 1–5° C. for 1 hr, the crystals were collected by filtration and dried to give the title compound (29.6 g, 0.083 mol, yield 82.9%, melting point: 156–160° C.).

EXAMPLE 12

Synthesis of 10-(3-chloro-1-azabicyclo[2.2.2]oct-3-ylmethyl)phenothiazine (Synthesis of compound [I])

10-(3-Hydroxy-1-azabicyclo[2.2.2]oct-3-ylmethyl)phenothiazine (63.4 g, 0.187 mol) and water (7.039 g, 0.390 mol) were added to monochlorobenzene (330 ml), and phosphorus oxychloride (59.8 g, 0.390 mol) was added dropwise at 65–75° C. The mixture was heated, reacted at 77° C. for 16 hr while bubbling the reaction mass with a nitrogen gas at about 160 ml/min, and the termination of the reaction was confirmed by HPLC.

Separately, 99% sodium hydroxide (47.3 g, 1.17 mol) was dissolved in water (165 ml) and the reaction mixture was added dropwise at about 55° C. for hydrolysis. The obtained organic layer was treated with active charcoal (3.3 g) and concentrated. The concentrate was crystallized with a mixed solution of monochlorobenzene (68 ml) and diglyme (66 ml). After aging at about 5° C. for 1 hr, the crystals were collected by filtration and dried to give the title compound (51.0 g, 0.143 mol, yield 76.3%, melting point:156–160° C.).

Differential Scanning Calorimetry (DSC)

The compounds [III] obtained in the above-mentioned Examples 4 and 6–8 were subjected to differential scanning calorimetry in an aluminum cell in a stream of nitrogen (50 ml/min) at 10° C./min while elevating the temperature from room temperature to 200° C. The results of each compound are shown in FIGS. 2–5, respectively.

EXAMPLE 13

Synthesis of 10-(3-chloro-1-azabicyclo[2.2.2]oct-3-ylmethyl)phenothiazine (Synthesis of compound [I])

10-(3-Hydroxy-1-azabicyclo[2.2.2]oct-3-ylmethyl) phenothiazine (132.0 g, 0.390 mol) and water (10.5 g, 0.585 mol) were added to monochlorobenzene (660 ml), and phosphorus oxychloride (119.6 g, 0.780 mol) was added dropwise at 65–75° C. The mixture was heated, reacted at 77° C. for 16 hr while bubbling the reaction mass with a nitrogen gas at about 160 ml/min, and the termination of the reaction was confirmed by HPLC.

Separately, 99% sodium hydroxide (94.5 g, 2.34 mol) was dissolved in water (330 ml) and the reaction mixture was added dropwise at about 55° C. for hydrolysis. The obtained organic layer was washed with water (330 ml), treated with active charcoal (6.6 g) and concentrated. The concentrate was crystallized with a mixed solution of monochlorobenzene (200 ml) and diglyme (132 ml). After aging at about 5° C. for 1 hr, the crystals were collected by filtration and dried to give the title compound (111.3 g, 0.312 mol, yield 80.0%, melting point: 156–160° C.).

EXAMPLE 14

Synthesis of (E)-10-(1-azabicyclo[2.2.2]oct-3-ylidenemethyl)phenothiazine (compound [A])

To a suspension of potassium tert-butoxide (11.78 g, 0.105 mol, 1.5 equivalents relative to starting material) in diglyme (117 g) was added 10-(3-chloro-1-azabicyclo [2.2.2]oct-3-ylmethyl)phenothiazine (25.00 g, 0.070 mol) and the mixture was stirred at room temperature for 1 hr 15 min. The temperature of the reaction mixture was raised to 70–80° C. over 2 hr while stirring. After 2 hr after temperature rise, the termination of the reaction was confirmed by HPLC. The HPLC data showed compound [A]:compound [B]:compound [C]=95.3:4.2:0.2 (mol %).

Water (125 ml) was added to the reaction mixture, and the mixture was heated until dissolution of the content. The mixture was cooled to 0–5° C., and the precipitated crystals were collected by filtration, washed and dried under reduced pressure to give the title compound (20.44 g, yield 91.1%). melting point: 165–169° C.

$^1$H-NMR(CDCl$_3$)δ: 7.05–6.99(4H, m), 6.88–6.80(4H, m), 6.08(1H, s), 3.73(2H, s), 2.98–2.86(5H, m), 1.62–1.48 (4H, m)

EXAMPLE 15

Synthesis of (E)-10-(1-azabicyclo[2.2.2]oct-3-ylidenemethyl)phenothiazine (compound [A])

A suspension of 96% potassium hydroxide (20.46 g, 0.350 mol, 5 equivalents relative to starting material) in diglyme (70 g) was heated to 100° C. and cooled to room temperature. Thereto was added 10-(3-chloro-1-azabicyclo [2.2.2]oct-3-ylmethyl)phenothiazine (25.00 g, 0.070 mol) and the temperature of the reaction mixture was raised stepwise to the final temperature of 70–80° C. while stirring. After 6 hr after temperature rise (24 hr after addition), the termination of the reaction was confirmed by HPLC. The HPLC data showed compound [A]:compound [B]:compound [C]=94.2:5.1:0.3 (mol %).

Water (75 ml) was added to the reaction mixture, and the mixture was heated until dissolution of the content. The mixture was cooled to 0–5° C., and the precipitated crystals were collected by filtration, washed and dried under reduced pressure to give the title compound (19.07 g, yield 85.0%). The melting point and $^1$H-NMR of the obtained compound were the same as in Example 14.

EXAMPLE 16

Synthesis of (E)-10-(1-azabicyclo[2.2.2]oct-3-ylidenemethyl)phenothiazine (compound [A])

To a suspension of potassium tert-butoxide (4.71 g, 0.042 mol, 3 equivalents relative to starting material) in monoglyme (87 g) was added 10-(3-chloro-1-azabicyclo [2.2.2]oct-3-ylmethyl)phenothiazine (5.00 g, 0.014 mol) and the mixture was stirred at room temperature. After 6 hr from the initiation of the reaction, the termination of the reaction was confirmed by HPLC. The HPLC data showed compound [A]:compound [B]:compound [C]=92.2:5.8:1.3 (mol %).

Water (100 ml) was added to the reaction mixture, and the mixture was heated until dissolution of the content. The mixture was cooled to 0–5° C., and the precipitated crystals were collected by filtration, washed and dried under reduced pressure to give the title compound (3.92 g, yield 86.8%). The melting point and $^1$H-NMR of the obtained compound were the same as in Example 14.

EXAMPLE 17

Synthesis of (E)-10-(1-azabicyclo[2.2.2]oct-3-ylidenemethyl)phenothiazine (compound [A])

To a suspension of potassium tert-butoxide (87.5 g, 0.78 mol) in diglyme (668 ml) was added 10-(3-chloro-1-azabicyclo-[2.2.2]oct-3-ylmethyl)phenothiazine (222.6 g, 0.624 mol) and the temperature of the reaction mixture was raised to 70–80° C. After 2 hr after temperature rise, the termination of the reaction was confirmed by HPLC. The HPLC data showed compound [A]:compound [B]:compound [C]=97.1:1.9:0.1 (mol %).

Water (668 ml) was added to the reaction mixture, and the mixture was heated until dissolution of the content. The mixture was cooled to 0–5° C., and the precipitated crystals were collected by filtration, washed and dried under reduced pressure to give the title compound (183.9 g, yield 92.0%). The melting point and $^1$H-NMR of the obtained compound were the same as in Example 14.

COMPARATIVE EXAMPLE 1

Synthesis of (E)-10-(1-azabicyclo[2.2.2]oct-3-ylidenemethyl)phenothiazine (compound [A])

To a suspension of 90% sodium ethoxide (15.88 g, 0.210 mol, 3 equivalents relative to starting material) in diglyme (70.3 g) was added 10-(3-chloro-1-azabicyclo[2.2.2]oct-3-ylmethyl)phenothiazine (25.00 g, 0.070 mol) and the mixture was stirred at room temperature for 1 hr 45 min. Diglyme (70.3 g) was added and the temperature of the reaction mixture was raised to 70–80° C. with stirring. After 27 hr after the initiation of the reaction, the termination of the reaction was confirmed by HPLC. The HPLC data showed compound [A]:compound [B]:compound [C]= 79.1:11.6:7.9 (mol %).

Water (40 ml) was added to the reaction mixture, and the mixture was heated until dissolution of the content. The mixture was cooled to room temperature, and the precipitated crystals were collected by filtration, washed and dried under reduced pressure to give the title compound (10.44 g, yield 46.3%). The melting point and $^1$H-NMR of the obtained compound were the same as in Example 14.

EXAMPLE 18

Synthesis of Mequitazine (E)-10-(1-Azabicyclo[2.2.2]oct-3-ylidenemethyl) phenothiazine (10.00 g, 0.0312 mol), acetic acid (2.25 g, 0.0374 mol) and 10% palladium carbon (2.00 g, water content 50%) were added to methanol (158 g) and the mixture was stirred under pressurization with hydrogen (3–5 kg/cm$^2$, hydrogen gas amount:equimolar amount relative to starting material) at 45–50° C. for 8 hr. The obtained reaction mixture was subjected to HPLC. As a result, the starting material was not detected but highly pure mequitazine was quantitatively obtained.

$^1$H-NMR(CDCl$_3$)δ: 7.19–7.15(4H, m), 6.95–6.89(4H, m), 3.89–3.85(2H, m), 3.08–3.02(1H, dd, J=13.6,10.0 Hz), 2.81–2.73(4H, m), 2.48–2.43(1H, dd, J=13.6, 2.4 Hz), 2.24 (1H, m), 1.88–1.86(1H, m), 1.60–1.55(2H, m), 1.41–1.36 (2H, m)

EXAMPLE 19

Synthesis of Mequitazine (E)-10-(1-Azabicyclo[2.2.2]oct-3-ylidenemethyl) phenothiazine (183.9 g, 0.574 mol), acetic acid (68.9 g, 1.15 mol) and 10% palladium carbon (37.0 g, water content 50%) were added to methanol (1290 ml) and the mixture was stirred under pressurization with hydrogen (3–5 kg/cm$^2$, hydrogen gas amount: equimolar amount relative to starting material) at 45–50° C. for 8 hr. The obtained reaction mixture was subjected to HPLC. As a result, the starting material was not detected but highly pure mequitazine was quantitatively obtained. The $^1$H-NMR of the obtained compound was the same as in Example 18.

COMPARATIVE EXAMPLE 2

Synthesis of (Z)-10-(1-azabicyclo[2.2.2]oct-3-ylidenemethyl)phenothiazine (compound [B])

10-(3-Chloro-1-azabicyclo[2.2.2]oct-3-ylmethyl) phenothiazine (30.0 g, 0.084 mol) and potassium tert-butoxide (18.9 g, 0.168 mol) were added to toluene (260 g), and the mixture was reacted by refluxing under heating for 8 hr.

Water (100 ml) was added to the reaction mixture, and an inorganic matter was removed into an aqueous layer. After partitioning, the organic layer was washed with water (100 ml) and treated with active charcoal (10.0 g) and alumina (10.0 g), followed by evaporation of the solvent. Methanol (95 g) was added to the concentrated residue for dissolution and the solution was cooled to 0–5° C. The precipitated crystals were collected by filtration, washed and dried under reduced pressure to give the title compound (11.9 g, yield 44.0%). melting point:149–153° C.

$^1$H-NMR(CDCl$_3$)δ: 7.08–7.04(4H, m), 6.90–6.86(4H, m), 6.20(1H, s), 3.37(2H, s), 2.95–2.69(5H, m), 1.85–1.72(4H, m)

COMPARATIVE EXAMPLE 3

Synthesis of Mequitazine (Z)-10-(1-Azabicyclo[2.2.2]oct-3-ylidenemethyl) phenothiazine (10.00 g, 0.0312 mol) obtained in Comparative Example 2, acetic acid (2.25 g, 0.0374 mol) and 10% palladium carbon (2.00 g, water content 50%) were added to methanol (158 g) and the mixture was stirred under pressurization with hydrogen (3–5 kg/cm$^2$, hydrogen gas amount:equimolar amount relative to starting material) at 45–50° C. for 8 hr, in the same manner as in Example 18. The obtained reaction mixture was subjected to HPLC. The results showed mequitazine:compound 2b (starting material)=51:49 (mol %).

The compounds obtained in Example 14 and Comparative Example 2 were subjected to X-ray crystal diffraction analysis, and the molecular structure was determined by a conventional method. The obtained molecular structures are shown in FIG. 1 and FIG. 2, respectively. The measurement conditions of the X-ray crystal diffraction and the measurement data obtained thereby are shown in the following.

Measurement Conditions

Measurement apparatus: Rigaku AFC7R

Light source: CuKα ray (λ=1.54178Å)

Temperature: 23.0° C.

Measurement data of compound of Example 14

Lattice constant: a=7.4085(9)Å, b=10.3915(7)Å, c=21.7777(6)Å,

β=98.789(6)°,

V=1656.9(2)Å$^3$,

Space group: P2$_1$/c(#14),

Z value: 4,

R factor: 0.043

Measurement data of compound of Comparative Example 2

Lattice constant: a=9.083(1)Å, b=15.853(1)Å, c=11.975(2)Å,

β=103.280(10)°,

V=1678.3(3)Å$^3$,

Space group: P2$_1$/n(#14),

Z value: 4,

R factor: 0.051

The comparison of Examples 14–17 and Comparative Example 1 reveals that elimination of hydrogen halide under the reaction conditions of the present invention leads to the production of highly pure compound [A] at a high yield. The comparison of Example 18 and Comparative Example 3 reveals that compound [B] does not allow easy progress of hydrogenation as in compound [A], and that, in the case of compound [B], hydrogenation requires addition of a hydrogenation catalyst.

According to the method of the present invention, 3-methylenequinuclidine oxide (compound [II]) can be obtained industrially and safely because, in Step 1, the reaction rate can be controlled and unstable dimsyl sodium can be reacted immediately after its formation. After the completion of Step 1, Step 2 is directly carried out without treatment of the reaction mixture or isolation of compound [II]. As a result, a decrease in the yield due to the isolation of compound [II], an influence of the reagent used in isolation in Step 1 or Step 2, and the like can be eliminated, thereby enabling production of compound [III] at a constantly high yield. By removing by-produced acidic gas and adding water in Step 3, compound [I] can be obtained efficiently. That is, the present invention can produce compound [I], which is useful as an intermediate for mequitazine, industrially, safely and efficiently.

According to the method of the present invention, moreover, (E)-10-(1-azabicyclo[2.2.2]oct-3-ylidenemethyl) phenothiazine (compound [A]) having a purity of not less than 85 mol % can be provided. By using this compound as a starting material, pharmaceutically useful mequitazine having various actions such as antihistaminic action, cholinergic action-inhibitory action, antiadrenergic action, neurosedative action, ataractic action, spasmolytic action and the like can be provided economically at a high purity and at a high yield.

This application is based on patent application Ser. Nos. 211310/1999 and 321786/1999 filed in Japan, the contents of which are hereby incorporated by reference.

What is claimed is:

1. A method for producing 10-(3-halogeno-1-azabicyclo[2.2.2]oct-3-ylmethyl)phenothiazine of the formula [I]

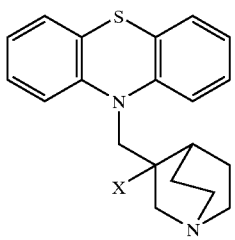

[I]

wherein X is a halogen atom, which comprises Step 1: adding an alkali metal compound to a mixture comprising dimethyl sulfoxide, 3-quinuclidinone or a salt thereof, and trimethyloxosulfonium halide to give 3-methylenequinuclidine oxide of the formula [II]

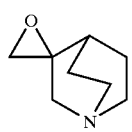

[II]

Step 2: reacting the obtained 3-methylenequinuclidine oxide with an alkali metal salt of phenothiazine to give a hydroxyl compound of the formula [III]

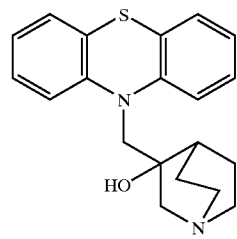

[III]

Step 3: reacting the hydroxyl compound or a hydrate thereof with a halogenation agent in a reaction solvent to give the phenothiazine compound of the formula [I].

2. The method of claim 1, wherein, in Step 1, the alkali metal compound is added intermittently.

3. The method of claim 1, wherein, in Step 1, the alkali metal compound is added intermittently as a solid or added dropwise as a suspension in a solvent inert to the alkali metal compound.

4. The method of claim 1, wherein, in Step 1, the mixture comprises a solvent inert to the reaction.

5. The method of claim 1, wherein, in Step 1, the alkali metal compound is an alkali metal hydride or alkali metal alkoxide.

6. The method of claim 1, wherein, in Step 1, the alkali metal compound is sodium hydride.

7. The method of claim 1, wherein, in Step 1, the trimethyloxosulfonium halide is trimethyloxosulfonium iodide.

8. The method of claim 1, wherein, in Step 2, the alkali metal salt of phenothiazine is a potassium salt or sodium salt of phenothiazine.

9. The method of claim 1, wherein Step 2 is successively carried out after Step 1.

10. The method of claim 1, wherein Step 3 further comprises removing a by-produced acidic gas from a reaction system.

11. The method of claim 10, wherein the by-produced acidic gas is removed from the reaction system by introducing an inert gas into the reaction system or by refluxing a reaction mixture under less than atmospheric pressure.

12. The method of claim 1, wherein, in Step 3, the hydroxyl compound is reacted with phosphorus oxychloride in monochlorobenzene while introducing a nitrogen gas into the reaction system.

13. The method of claim 1, further comprising adding water to the reaction system in Step 3.

14. The method of claim 1, wherein, in Step 3, the halogenation agent is phosphorus oxychloride and Step 3 further comprises adding water to the reaction system in a 0.1- to 1.25-fold molar amount relative to phosphorus oxychloride.

15. A hydrate of a hydroxyl compound of the formula [III]

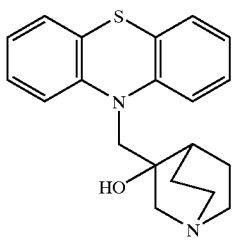

[III]

16. A crystal of a hydroxyl compound of the formula [III]

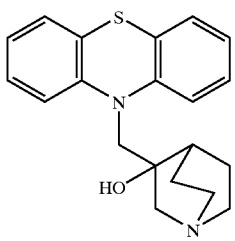

[III]

having a peak in 143–145° C. in a differential scanning calorimetric curve.

17. A method for producing a phenothiazine compound of the formula [I]

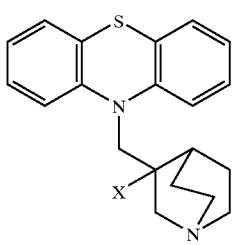

[I]

wherein X is a halogen atom, which comprises reacting a hydroxyl compound of the formula [III]

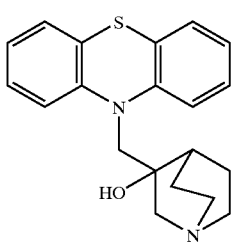

[III]

or a hydrate thereof with a halogenation agent and water.

18. The method of claim 17, further comprising removing a by-produced acidic gas from a reaction system.

19. The method of claim 18, wherein the by-produced acidic gas is removed from the reaction system by introducing an inert gas into the reaction system or by refluxing a reaction mixture under less than atmospheric pressure.

20. (E)-10-(1-Azabicyclo[2.2.2]oct-3-ylidenemethyl)phenothiazine of the formula [A]

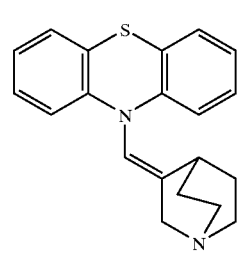

[A]

having a purity of not less than 85 mol %.

21. A method for producing (E)-10-(1-azabicyclo[2.2.2]oct-3-ylidenemethyl)phenothiazine comprising subjecting 10-(3-halogeno-1-azabicyclo[2.2.2]oct-3-ylmethyl)phenothiazine of the formula [I]

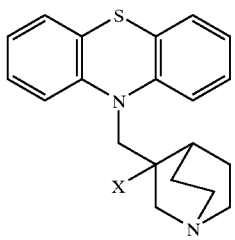

[I]

wherein X is a halogen atom, to elimination of hydrogen halide in glyme in the presence of at least one kind of a base selected from the group consisting of potassium hydroxide and potassium alkoxide.

22. The method of claim 21, wherein the base is potassium hydroxide.

23. The method of claim 21, wherein the base is potassium tert-butoxide.

24. The method of claim 21, wherein the 10-(3-halogeno-1-azabicyclo[2.2.2]oct-3-ylmethyl)phenothiazine is 10-(3-chloro-1-azabicyclo[2.2.2]oct-3-ylmethyl)phenothiazine.

* * * * *